US 9,861,737 B2

(12) United States Patent
Mehta

(10) Patent No.: US 9,861,737 B2
(45) Date of Patent: *Jan. 9, 2018

(54) NASAL RINSE TIP

(71) Applicant: Ketan C. Mehta, Santa Rose, CA (US)

(72) Inventor: Ketan C. Mehta, Santa Rose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/485,171

(22) Filed: Sep. 12, 2014

(65) Prior Publication Data

US 2015/0005714 A1    Jan. 1, 2015

Related U.S. Application Data

(63) Continuation of application No. 13/708,681, filed on Dec. 7, 2012, now Pat. No. 8,834,433, which is a continuation of application No. 12/567,518, filed on Sep. 25, 2009, now Pat. No. 8,343,114.

(51) Int. Cl.
*A61M 3/02* (2006.01)

(52) U.S. Cl.
CPC .......... *A61M 3/0262* (2013.01); *A61M 3/025* (2013.01); *A61M 3/0279* (2013.01); *A61M 2205/3334* (2013.01); *A61M 2210/0618* (2013.01)

(58) Field of Classification Search
CPC .. A61M 3/0262; A61M 3/0279; A61M 3/025; A61M 2205/3334; A61M 2210/0618
IPC .................................................... A61M 3/0262
See application file for complete search history.

(56) References Cited

U.S. PATENT DOCUMENTS

| | | | |
|---|---|---|---|
| 2,135,052 A | * | 11/1938 | Rose ...................... A61H 35/04 604/24 |
| 3,186,645 A | | 6/1965 | Eberlein |
| 3,471,092 A | | 10/1969 | Hickey |
| 4,650,094 A | | 3/1987 | Werding |
| 5,116,311 A | | 5/1992 | Löfstedt |
| 5,301,846 A | | 4/1994 | Schmitz |
| 5,505,193 A | | 4/1996 | Ballini et al. |
| 5,649,530 A | | 7/1997 | Ballini |
| 5,806,723 A | | 9/1998 | DuBose |
| 5,906,198 A | | 5/1999 | Flickinger |
| 6,234,365 B1 | | 5/2001 | Bougamont et al. |
| 6,293,436 B2 | | 9/2001 | Faughnder et al. |

(Continued)

FOREIGN PATENT DOCUMENTS

| FR | 2 387 047 | 11/1978 |
|---|---|---|
| JP | 2005-287669 A | 10/2005 |

(Continued)

OTHER PUBLICATIONS

Supplementary European Search Report in Application No. EP 12 77 7087.3, mailed May 12, 2015, 8 pages.

(Continued)

*Primary Examiner* — Bradley Osinski
(74) *Attorney, Agent, or Firm* — Kelley Drye & Warren LLP

(57) ABSTRACT

A device for nasal lavage is described. The device ejects a gentle flow of fluid under pressure. The fluid stream provides a high quantity of fluid at low pressure. The low pressure fluid stream is more comfortable for a user than a high pressure fluid stream that is delivered by some types of pressurized cans of solution.

22 Claims, 8 Drawing Sheets

(56) References Cited

U.S. PATENT DOCUMENTS

| | | | |
|---|---|---|---|
| 6,520,384 B2 | 2/2003 | Mehta | |
| 6,644,305 B2* | 11/2003 | MacRae | A61M 15/0086 128/200.14 |
| 7,302,948 B2 | 12/2007 | Anderson | |
| 8,343,114 B2* | 1/2013 | Mehta | A61M 3/0262 604/275 |
| 8,801,667 B2 | 8/2014 | Taylor et al. | |
| 8,834,433 B2* | 9/2014 | Mehta | A61M 3/025 604/275 |
| 2002/0158089 A1 | 10/2002 | Mehta | |
| 2004/0068222 A1* | 4/2004 | Brian | A61M 11/06 604/65 |
| 2004/0116892 A1 | 6/2004 | Burroughs et al. | |
| 2005/0098172 A1 | 5/2005 | Anderson | |
| 2005/0210572 A1 | 9/2005 | Fogel | |
| 2006/0162722 A1 | 7/2006 | Boehm et al. | |
| 2006/0237003 A1* | 10/2006 | Rasor | A61H 33/14 128/200.24 |
| 2007/0060868 A1 | 3/2007 | Tsutsui | |
| 2007/0175917 A1* | 8/2007 | Bonney | B05B 11/0064 222/14 |
| 2008/0008979 A1 | 1/2008 | Thomas et al. | |
| 2008/0154183 A1 | 6/2008 | Baker et al. | |
| 2008/0312674 A1 | 12/2008 | Chen et al. | |
| 2009/0281454 A1 | 11/2009 | Baker et al. | |
| 2010/0012680 A1 | 1/2010 | Canfield et al. | |
| 2011/0077603 A1 | 3/2011 | Mehta | |
| 2011/0144588 A1 | 6/2011 | Taylor et al. | |
| 2011/0155750 A1 | 6/2011 | Bernstein et al. | |
| 2011/0319840 A1 | 12/2011 | Hair | |
| 2012/0277675 A1 | 11/2012 | Mehta | |
| 2013/0197450 A1 | 8/2013 | Mehta | |
| 2014/0039411 A1 | 2/2014 | Mehta | |
| 2015/0314061 A1 | 11/2015 | Mehta | |

FOREIGN PATENT DOCUMENTS

| | | |
|---|---|---|
| KR | 10-2000-0066190 A | 11/2000 |
| WO | WO 02/07668 A1 | 1/2002 |

OTHER PUBLICATIONS

OCEAN Complete® [online]. Fleming Pharmaceuticals, 2009 [retrieved on Dec. 12, 2009]. Retrieved from the Internet: <URL: http://flemingpharma.com/content/view/141/140/, 2 pages.

OCEAN Ultra® Sterile Saline Nasal Mist [online]. Fleming Pharmaceuticals, 2009 [retrieved on Dec. 29, 2009]. Retrieved from the Internet: <URL: http://flemingpharma.com/content/view/84/81/, 1 page.

SinuCleanse Squeeze™ [online]. Med-Systems, Inc., 2008 [retrieved on Dec. 29, 2009]. Retrieved from the Internet: <URL: http://www.sinucleanse.com/product/squeeze.htm, 3 pages.

Authorized Officer Ji Myong Nho, International Search Report and Written Opinion in PCT/US2010/050434, mailed Jun. 21, 2011, 9 pages.

Authorized officer Agnès Wittmann-Regis, International Preliminary Report on Patentability in PCT/US2010/050434, mailed Apr. 5, 2012, 6 pages.

Authorized officer Cheol Soo Lee, International Search Report and Written Opinion in PCT/US2012/035616, mailed Nov. 26, 2012, 9 pages.

Authorized officer Philippe Bécamel, International Preliminary Report on Patentability in PCT/US2012/035616, mailed Nov. 7, 2013, 6 pages.

Communication pursuant to Article 94(3) EPC in Application No. EP 12 777 087.3, mailed Feb. 19, 2016, 6 pages.

Official Action in Israel Application No. 229096, dated Feb. 15, 2017, 4 pages.

* cited by examiner

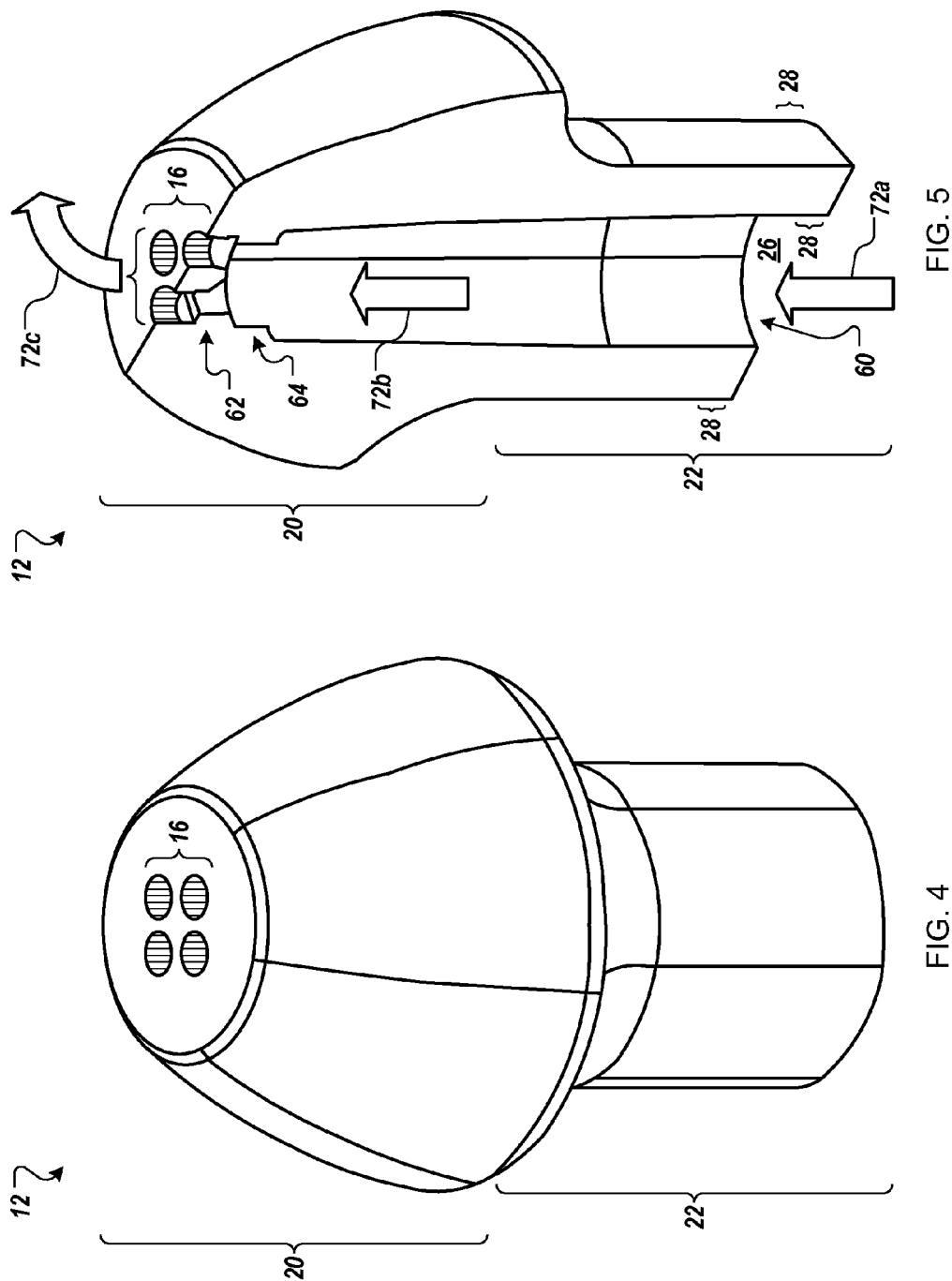

NASAL RINSE TIP

CROSS-REFERENCE TO RELATED APPLICATIONS

This is a continuation of U.S. application Ser. No. 13/708,681, filed Dec. 7, 2012, which is a continuation of U.S. application Ser. No. 12/567,518, filed Sep. 25, 2009 (now U.S. Pat. No. 8,343,114). The disclosures of the prior applications are considered part of and are incorporated by reference in the disclosure of this application.

BACKGROUND

This invention relates to nasal lavage.

People in many parts of the world perform nasal cleansing (or nasal irrigation) using a neti pots or other products on a routine basis, like brushing their teeth or showering. Nasal cleansing is even incorporated into some forms of yoga practice, such as in Jala neti. Jala neti is a Sanskrit term that refers to cleansing and means "water cleansing." Often, the solution for rinsing the nasal passages using a neti pot or other product is a saline solution. Some people use nasal rinsing to reduce allergies, improve breathing, eliminate post-nasal drip or sinus infections, moisten dry nasal passages, avoid catching a cold or to generally improve one's health. Some people also claim that nasal lavage improves ones vision by cleaning the tear ducts, improves the sense of smell and improves ones sense of taste.

Some problems with nasal lavage products can be that the canisters containing rinse solution may be under excessive pressure, causing solution flow to be somewhat uncomfortable during use.

SUMMARY

The device described herein is configured for ease of use, controllability of the solution exiting the device, and comfort for the user.

In one aspect, a device is described that ejects fluid. The device includes a body surrounding a chamber, wherein the body is configured to resist a change in shape when a pressure change occurs within the body, a valve, an actuator having a fluid path that is fluidly connected to the chamber when the valve is in an open position and a tip, wherein the tip is configured to attenuate a pressure of fluid flow exiting the actuator.

Embodiments of the device can include one or more of the following features. A tube can be within the chamber and connected to the valve. The device can include a bag, wherein the bag comprises a flexible material, is within the body, and surrounds the tube and an interior of the bag is hermetically sealed from a space between the body and an exterior of the bag. The tip can be formed of a flexible material. The tip can be formed of silicone. The actuator can be formed of a material that is more rigid than the tip. The tip can have a distal portion and a proximate portion, an aperture in the proximate portion defines an interior of a collar that surrounds a portion of the actuator, the distal portion has one or more apertures and a stop, the stop of the tip can be positioned to block the fluid flow exiting the aperture and causes the fluid flow to be redirected toward the proximate portion of the tip. The tip can have an exterior circumference of less than 1.5 cm. The device can have one or more apertures in the distal portion include at least four apertures and the at least four apertures surround the stop. The device can have a canal between the aperture that defines an interior of the collar and the stop tapers inwardly from the collar to the stop. The exterior of the tip can taper outwardly between the distal portion and the proximate portion. The exterior can be curved between the distal portion and the proximate portion. The device can include a sterile saline solution within the body, wherein when the body is held in an upright orientation with the tip furthest from ground and no obstructions are beyond the tip to affect the fluid flow, actuating the actuator causes the fluid flow to exit the actuator and exit the tip in a stream, wherein an entirety of the stream projects up and away from the tip and curves back toward the ground within 6 centimeters of the tip, without the tip the fluid flow exits the actuator in a stream that extends away from the actuator along a substantially straight and unchanging trajectory at 6 centimeters from the actuator. A canal can be between the at least four apertures and the aperture that defines the interior of the collar and each of the four apertures is fluidly connected to an annular chamber, and the annular chamber is fluidly connected to the canal. A greatest extent of the at least four apertures together can be greater than an external circumference of the annular chamber. The device can include a circular chamber between the canal and the annular chamber. The external circumference of the annular chamber can be greater than a circumference of the circular chamber. The circumference of the circular chamber can be less than a minimum circumference of the canal by at least 0.1 mm. The canal can have an internal volume of at least 0.47 cm$^3$. An area of the apertures in the distal portion of the tip can be greater than an area of the circular chamber. The tip can have one or more grooves extending from an open proximal portion and at least 50% of a length of the tip. The tip can have an aperture along a side surface of the tip that is fluidly connected to an interior channel extending from the open proximal portion. The tip can have two apertures across from one another, the apertures and the interior channel configured in the shape of a T.

The devices described herein may include one or more of the following advantages. A gentle flow of solution can be expelled from a soft or compliant tip. The tip material can be comfortable against a user's nose. The gentle flow can be used to irrigate or cleanse a tissue, such as the interior of a nostril. The gentle flow of fluid can be less irritating or painful than a more intense stream of fluid. A user is more likely to use a gentle flow of fluid and treatment compliance can be higher. This can result in a more effective treatment of the patient.

The details of one or more implementations of the invention are set forth in the accompanying drawings and the description below. Other features, objects, and advantages of the invention will be apparent from the description and drawings, and from the claims.

DESCRIPTION OF DRAWINGS

FIGS. 4 and 5 are schematic perspective views of a tip used on the device.

Like reference symbols in the various drawings indicate like elements.

DETAILED DESCRIPTION

Figure 1:
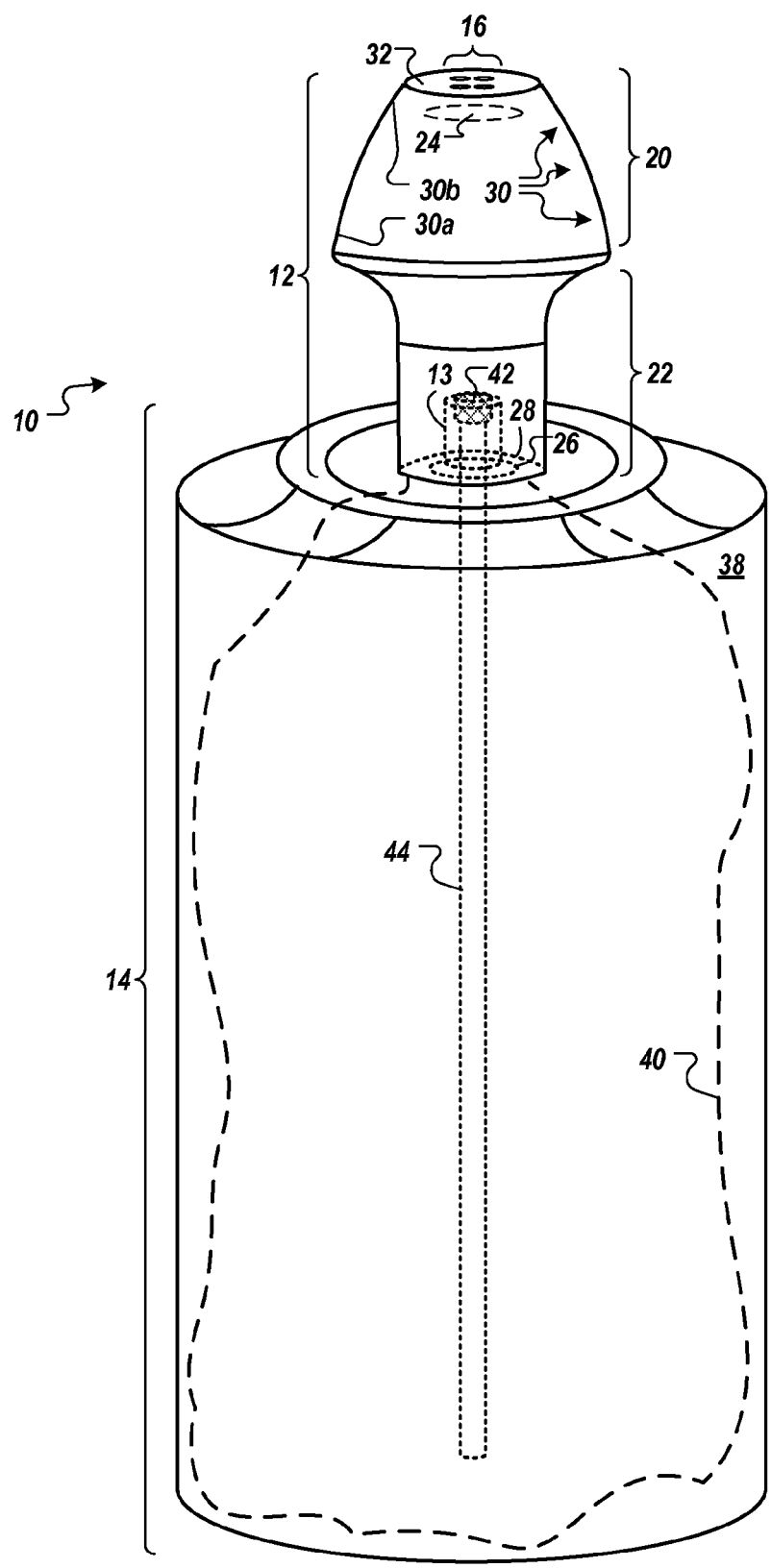
FIG. 1 is a schematic perspective view of a device.

Referring to FIG. 1, a fluid ejection device 10 is shown. The fluid ejection device 10 includes a tip 12 that is attached to an actuator 13, which in turn is attached to a body 14. The body 14 can be, for example, a container of saline solution or any other fluid suitable for irrigating nasal cavities. The fluid ejection device 10 can be used, for example, to provide nasal rinsing (or irrigation or nasal lavage), such as to treat allergies, improve breathing, eliminate post-nasal drip or sinus infections, moisten dry nasal passages, etc. The tip 12 can attenuate the pressure of fluid stored in the body 14, dispensing fluid at a significantly more gentle pressure but at a higher volume or flow rate. The gentle pressure can be sufficient pressure to delivery a flow of fluid to nasal tissue without the pressure being so great as to apply sufficient pressure to the tissue to displace the tissue.

In some implementations, the body 14 can be a fluid container (e.g., can, canister, bottle, etc.) having bag-on valve technology where there is a bag inside the can and the valve can release the solution when the actuator is actuated, i.e., pressed. In some implementations, the fluid ejection device 10 can be used on a plastic bottle which is pressurized and has a solution inside the bottle. In some implementations, the fluid delivery is from an aerosol type can, but the fluid is ejected from the tip 12 in a fluid stream, rather than an aerosol.

The tip 12 can be operable to provide an attenuated pressure of fluid flow from the body 14. For example, the body 14 can be a commercially-available, pressurized container of saline solution or other sterile fluid which ordinarily dispenses fluid at a pressure that may be unsuitable, uncomfortable or unsafe for use in nasal lavage. As such, the tip 12 can include features that facilitate the delivery of fluid in a generally more gentle stream through at least one (e.g., about four or more) apertures 16 at the end of the tip 12. Fluid flow can be controlled, for example, by pressing the tip 12. In some implementations, the tip 12 can be pressed straight against the nose, allowing fluid to flow from the tip. In other implementations, pressing the tip 12 from the side can control fluid flow.

The tip 12 includes a distal portion 20 and a proximate portion 22. The distal portion 20 of the tip 12 can be approximately conically shaped, with a convex curved surface leading from the apertures 16 toward the proximate portion 22. In other implementations, the distal portion 20 can be approximately gumdrop- or mushroom-shaped. The tip 12 can include a tapered surface 30 that permits the tip 12 to conform to nostrils of different sizes. Specifically, the exterior of the tip 12 can be tapered outwardly along the distal portion 20. In other words, the tip 12 tapers from a wide portion 30a up to a narrow portion 30b, where the narrow portion 30b is closer to the apertures 16 than to the proximate portion 22. Moreover, the tip 12 can be sized to prevent the wide portion 30a from extending all the way into the user's nostril.

The distal portion 20 can contain the features of the tip 12 that facilitate fluid flow, at an attenuated pressure, from the apertures 16. A stop 24 can be the ceiling of the interior fluid canal within the tip 12, positioned to block the fluid flow exiting the body 14, and causing the fluid flow to be redirected toward the proximate portion 22 of the tip 12. As a result, fluid can "pool" or otherwise accumulate inside the tip 12 and be dispensed at a reduced pressure through the apertures 16, while being replenished from fluid from the body 14 which dispenses at a higher pressure.

The apertures 16 can be arranged, for example, on a mesa 32 at the end of the distal portion 20. As depicted, the mesa 32 has a relatively flat surface, but other shapes (e.g., a convex shape) can be used that are effective at distributing the apertures 16 for efficient dispensing of fluid.

An aperture 26 in the proximate portion 22 can define the interior boundary of a collar 28 that surrounds, and securely attaches to, a portion of the actuator 13. In some implementations, if the actuator 13 is relatively small (e.g., a spray-paint can's spray button size), the aperture 26 can attach directly to the body 14. For example, the collar 28 can provide a snap-fit, screw-fit, or other such sealed connection between the proximate portion 22 (of the tip 12) and the body 14. However, when the actuator 13 is significantly larger, as it can be in some implementations, the tip 12 can attach directly to the actuator 13. In general, the tip 12 can be manufactured in various sizes or be adjustable to fit any size actuator 13 or body 14.

To aid in comfort of use, the tip 12 can be formed of a flexible material, such as silicone or some another soft, flexible material (e.g., plastic, rubber, non-permeable cloth, etc.) that can generally feel comfortable against the user's skin. The tip 12 can have an exterior circumference of less than 2 cm, such as less than 1.5 cm, allowing it to fit snugly against, but not extend all the way into, an average sized user's nostril. The actuator 13 can be formed of a material that is significantly more rigid than the tip 12. As such, the actuator 13 can hold its shape during use.

The body 14 surrounds a chamber 38. The body 14 can be configured to resist a change in shape when pressure changes occur within the body 14 due to the contents of the chamber 38. For example, if the body 14 is formed of a generally rigid material (e.g., metal, such as steel or aluminum, plastic, such as a recyclable resin, such as polyethylene, polycarbonate or polypropylene, etc.), the body 14 can retain its shape when the chamber 38 is fully-pressurized (e.g., full of fluid), partially-pressurized, and essentially un-pressurized (e.g., when the fluid is essentially depleted).

In some implementations, the body 14 can include a bag 40 inside the chamber 38. The bag 40 can contain the fluid stored by the body 14 and can be formed of a flexible material, such as a pliable plastic. Further, the bag 40 can be hermetically sealed from the space between the body 14 and an exterior of the bag 40. As a result, using the bag 40 or a device similar to the bag-on valve technology (e.g., a pressurized can or pressurized bottle) can provide a sterile solution suitable for use in a body cavity or with a wound.

As will be described in more detail below, the body 14 can include a valve 42 and a tube 44. The valve 42, such as any type of valve used on spray cans, can be used to control (e.g., start, stop, etc.) the flow of fluid from the chamber 38 to the tip 12. The fluid can flow through the tube 44 which can extend into the bottom end of the body 14, or the end that is most distal from the tip 12.

Figure 2:
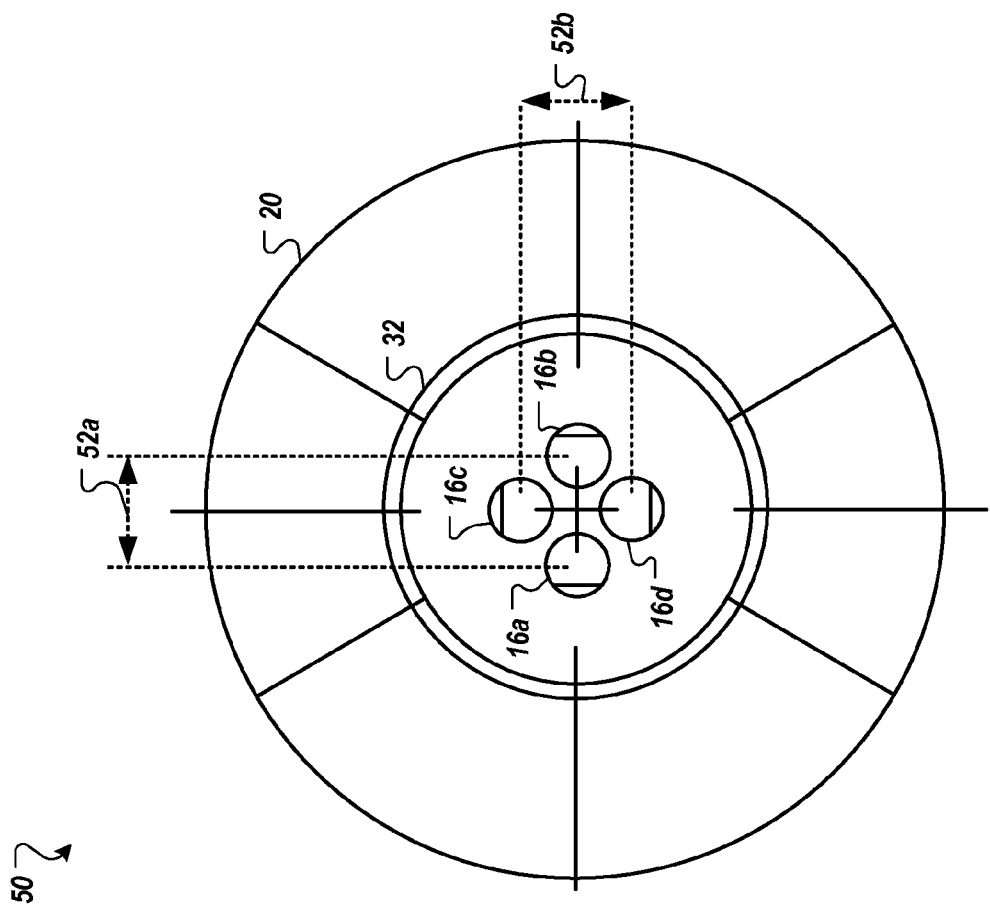

Referring to FIG. 2, an exemplary top view 50 of the fluid ejection device 10 is shown. The top view 50 shows the apertures 16a-16d arranged on the mesa 32, located on the tip of the distal portion 20. As depicted in FIG. 2, in some implementations, the centers of any pair of adjacent apertures 16a-16d are spaced at between about 1 and 4 millimeters, such as about 3 millimeters, as shown by distances 52a and 52b. Specifically, the distance 52a corresponds to the distance between the centers of apertures 16a and 16b.

Similarly, the distance 52b corresponds to the distance between the centers of apertures 16c and 16d. The tip 12 can have an exterior circumference of less than 1.5 cm.

The diameters of the apertures 16a-16d can be any value (e.g., between about 1 and 2 millimeters, such as about 1.5 millimeters) such that, for example, the combination of the group of apertures 16a-16d produces a sufficient stream when the fluid ejection device 10 is in use. In some implementations, as the number of apertures is increased, the diameter of the apertures generally can be reduced.

In some implementations, different sizes of the apertures 16a-16d and/or other spacing between the apertures 16a-16d can be used, and fewer or additional apertures 16a-16d can exist, with varying distances between any of the apertures 16a-16d. In some implementations, distances 52a and 52b may be less than, or greater than, 3 millimeters. In some implementations, there are two, three, four, five or six apertures in the tip 12. The total cross sectional area of the apertures 16a-16d is generally less than the cross sectional area at any cross section of the canal 60 (e.g., having diameters 66 described with respect to FIG. 3) carrying the supply of fluid through the tip 12.

Figure 3:
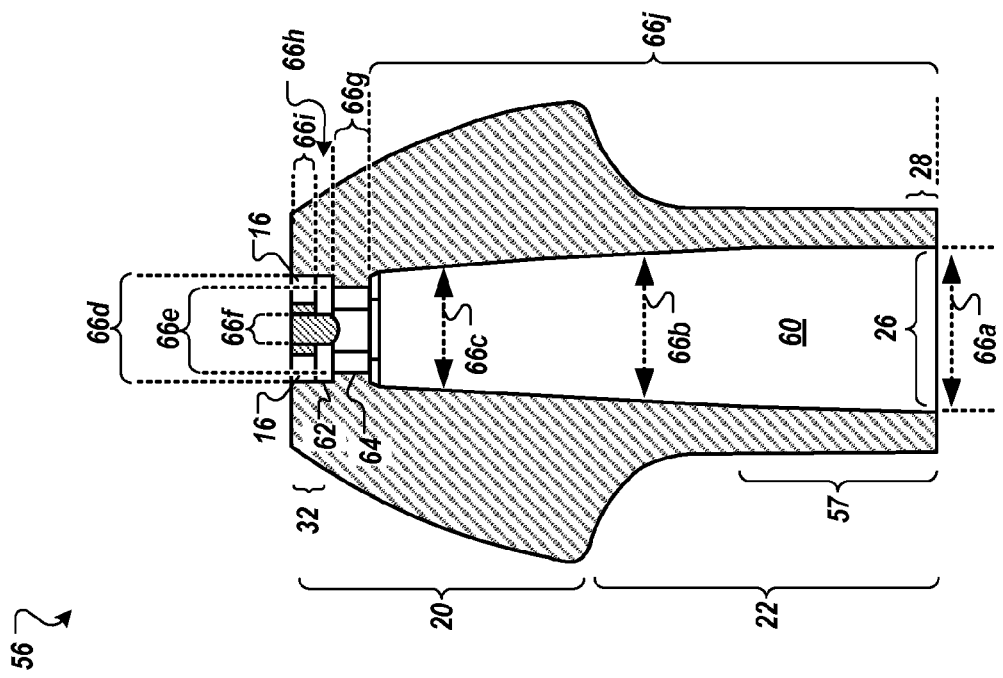
FIGS. 2 and 3 are a schematic top view and a schematic plan view of a tip used on the device.

Referring to FIG. 3, an exemplary side cross-section view 56 of the fluid ejection device 10 is shown. The view 56 shows the tapered shape of the tip 12, including the tapered surface 30 that extends along the distal portion 20 toward its intersection with the proximate portion 22. The view 56 further shows a cross-section of the features of the interior of the tip 12.

Fluid can flow through the tip 12 by entering a base area 57. For example, the base area 57 can include the collar 28 that serves as the connection point between the tip 12 and the actuator 13 and some adjacent region of the tip 12, such as a lower third of the tip. The collar 28 can surround or fit over a portion of the actuator 13, such as the portion of the actuator 13 from which fluid can flow. Fluid dispensed from within the chamber 38 can flow through the base area 57 and through the interior of the tip 12, exiting through the most distal end of the distal portion 20. In some implementations, the fluid can flow through the tube 44 and valve 42 (see FIG. 1).

The view 56 further shows internal features of the tip 12. A canal 60 in the interior of the tip 12 can provide fluid connectivity between the chamber 38 (e.g., via the actuator 13) and the apertures 16. Specifically, the canal 60 can extend from (and define the shape of) the aperture 26, defining the interior of the collar 28 The canal 60 can extend to, and be fluidly connected to, an annular chamber 62. In some implementations, a circular or cylindrical chamber 64 can exist, and be fluidly attached to, annular chamber 62 and canal 60. The canal 60 and the chambers 62 and 64 can work in combination, for example, based on their dimension, to attenuate the pressure of the fluid received from the body 14 that flows through and exits the tip 12. For example, the fluid entering the tip 12 can generally pool within the canal 60, and the chambers 62 and 64 can facilitate the flow of the fluid through the tip 12 at suitable pressure through the apertures 16. For instance, the shape and size of the chambers 62 and 64 can restrict the flow of fluid to a volume that is ideal for delivery to the apertures 16.

Various dimensions of components of the tip 12 can exist. For example, the canal 60 can have a tapered shape, having dimensions that include, for example, a diameter 66a of in the range between about 5 and 9 mm, such as about 7 mm at the aperture 26, a diameter 66b of in the range between about 5 and 7 mm, such as about 6 mm roughly halfway up through the canal 60, and an even smaller diameter 66c such as in the range between about 4 and 6 mm, such as about 5.5 mm or less approaching the apertures 16. The annular chamber 62 can have, for example, an outer diameter 66d equal to or less than 66c, such as in the range between about 4 and 5.2 mm, such as about 4.6 mm and an inner diameter 66f of in the range between about 1 and 1.5 mm, such as about 1.3 mm. The circular chamber 64 can have a diameter 66e equal to or less than that of diameter 66c in the range between about 3 and 5 mm, such as about 3.7 mm. In some implementations, the diameter 64 is less than the outer diameter of chamber 62. The diameters 66a-66f are just examples, as other diameters can be used in other implementations.

Various other dimensions of components of the tip 12 can exist. For example, the circular chamber 64 can have a thickness 66g in the range between about 1 and 2 mm, such as about 1.5 mm. The annular chamber 62 can have a thickness 66h in the range between about 0.5 and 1.2 mm, such as about 0.8 mm. The region between the mesa 32 and the stop 24 at the end of the distal portion 20 can have a thickness 66i in the range between about 0.8 and 1.2 mm such as about 1 mm. The canal 60 can have a length 66j in the range of between about 20 and 30 mm, such as about 25 mm. These thicknesses and lengths can vary in other implementations; however the side wall integrity of the tip 12 needs to be maintained.

Internal features of the tip 12 can vary in size and proportion to each other, the advantages of which can include better control of pressure attenuation. For example, in some implementations, the external circumference of the annular chamber 62 can be greater than the circumference of the circular chamber 64. In some implementations, the greatest extent of the apertures 16 (e.g., the sum of the surface areas of the apertures 16) can be greater than an external circumference of the annular chamber 62. In some implementations, the circumference of the circular chamber 64 is less than the minimum circumference of the canal 60 by in the range between 0.5 mm and 1.5 mm, such as at least about 0.1 mm. In some implementations, the canal 60 can have an internal volume of in the range between 0.3 cm$^3$ and 0.5 cm$^3$, such as at least about 0.4 cm$^3$. In some implementations, the combined area of the apertures 16 in the distal portion 20 of the tip 12 can be greater than an area of the circular chamber 64.

In some implementations, the total cross sectional area of apertures 16 is greater than the cross sectional area of the valve 42. Without being bound to any particular theory, liquid exits from chamber 38 at a high pressure, such as at a pressure greater than about 10 psi, such as in the range of 20 and 200 psi, such as at a pressure of greater than about 30 psi and enters canal 60 directed toward the apertures 16. The high pressure fluid contacts an end wall (e.g., the stop 24), which redirects the fluid toward aperture 26. Some fluid exits apertures 16 while canal 60 fills with fluid. Once the canal 60 fills, because the overall effective area of the apertures 16 area is greater than the valve 42 exit area in combination with the availability of fluid in the canal 60, the pressure of fluid exiting the chamber 38 is attenuated and the fluid exits the apertures 16 in a gentle contiguous stream.

Referring to FIG. 4, a perspective view of the fluid ejection device 10 is shown. Although the implementation shown in FIG. 4 includes four apertures 16 of the same size, other implementations can include more (or fewer) of the apertures 16. Further, the apertures 16 can have various sizes and spacing, for example, as can be determined through experimentation to deliver a stream of fluid more suitable for nasal lavage.

In some implementation, various models of the fluid ejection device 10 can exist, each having the advantage of a different configuration of apertures 16. For example, some users may prefer using a specific "Model X" over "Model Y" because of a difference in operation or "feel" of each, such as a noticeable difference in the strength of the stream of fluid from each. In some implementations, additional versions of the fluid ejection device 10 can have significantly larger tips 12 (e.g., for adults with significantly larger nostrils) or significantly smaller tips 12 (e.g., for babies or toddlers). As such, different models or versions of the fluid ejection device 10 can be produced.

Although implementations of the tip 12 and the fluid ejection device 10 are generally intended for human use, other implementations can include models or versions that are intended to use for animals, such as pets or livestock.

Referring to FIG. 5, a cross-section of a perspective view of the fluid ejection device 10 is shown. The view shows half of the tip 12 exposed, and as such exposes half of the distal portion 20 and the proximate portion 22, as well as revealing the canal 60.

Fluid can flow through the tip 12 in the direction indicated by arrows 72a-72c. Specifically, fluid from the body 14 can enter the tip 12, as indicated by arrow 72a. Fluid entering the tip 12 does so through the aperture 26, as defined by the inner dimension of the collar 28. Fluid flows through the canal 60, on the interior of the tip 12, as indicated by arrow 72c. Fluid exits the tip 12 at the apertures 16, as indicated by arrow 72c. Before reaching the apertures 16, the fluid can flow through the annular chamber 62, the circular chamber 64, and any other chambers not depicted.

Figure 6:
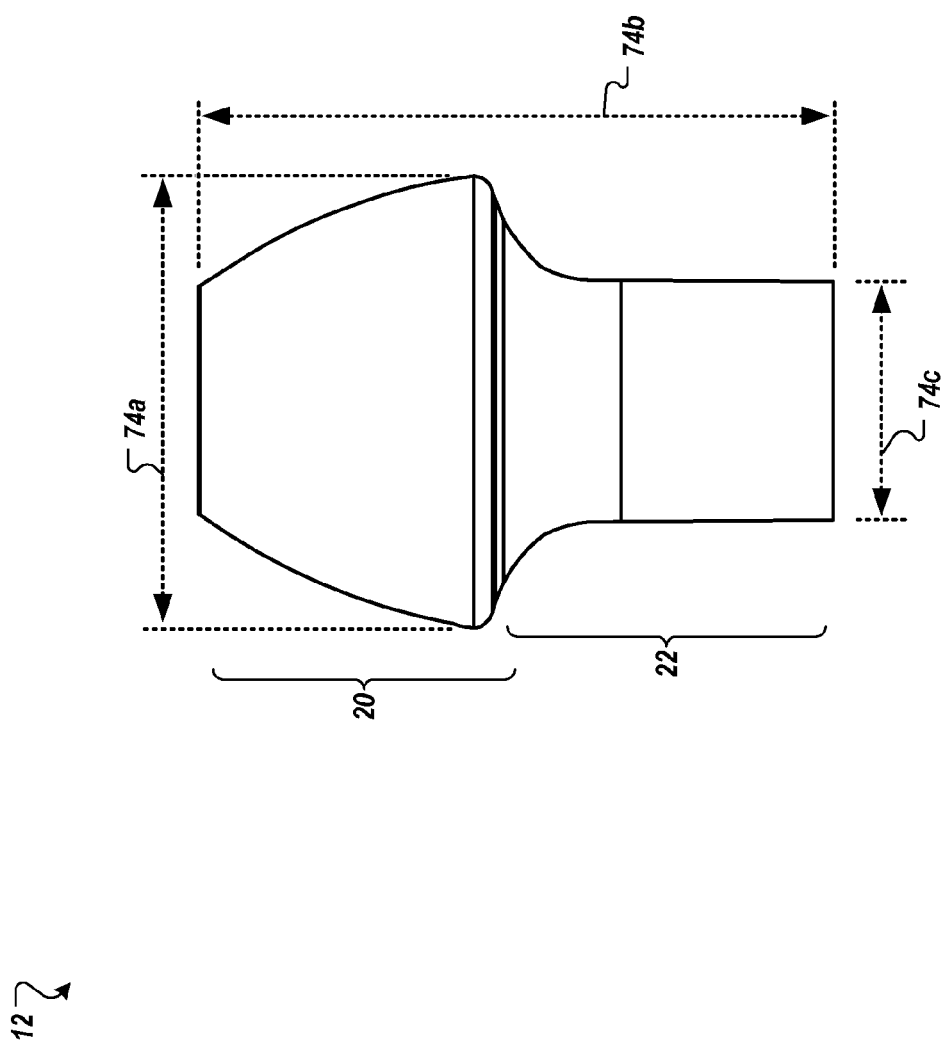
FIG. 6 is a schematic side view of the tip.

Referring to FIG. 6, exemplary dimensions of the tip 12 are shown. For instance, in some implementations, the diameter 74a of the widest part of the distal portion 20 (and of the tip 12 itself) can be, for example, in the range between 15 and 25 mm, such as about 20 mm or any other size that is suitable for use with human nostrils. In some implementations, the length 74b of the tip 12 can be, for example, in the range between 20 and 40 mm, such as about 30 mm, or any other suitable length. For instance, longer tips 12 can be necessary to fit different types of actuators 14, depending on the size of any exposed tube 44 and valve 42. The diameter 74c of the proximate portion 22 of the tip 12 can be, for example, in the range between 7 and 14 mm, such as about 10 mm, or any other size that can enable the tip 12 to fit the portion of the actuator 13 or body 14 to which the tip 12 is attached.

Figure 7:
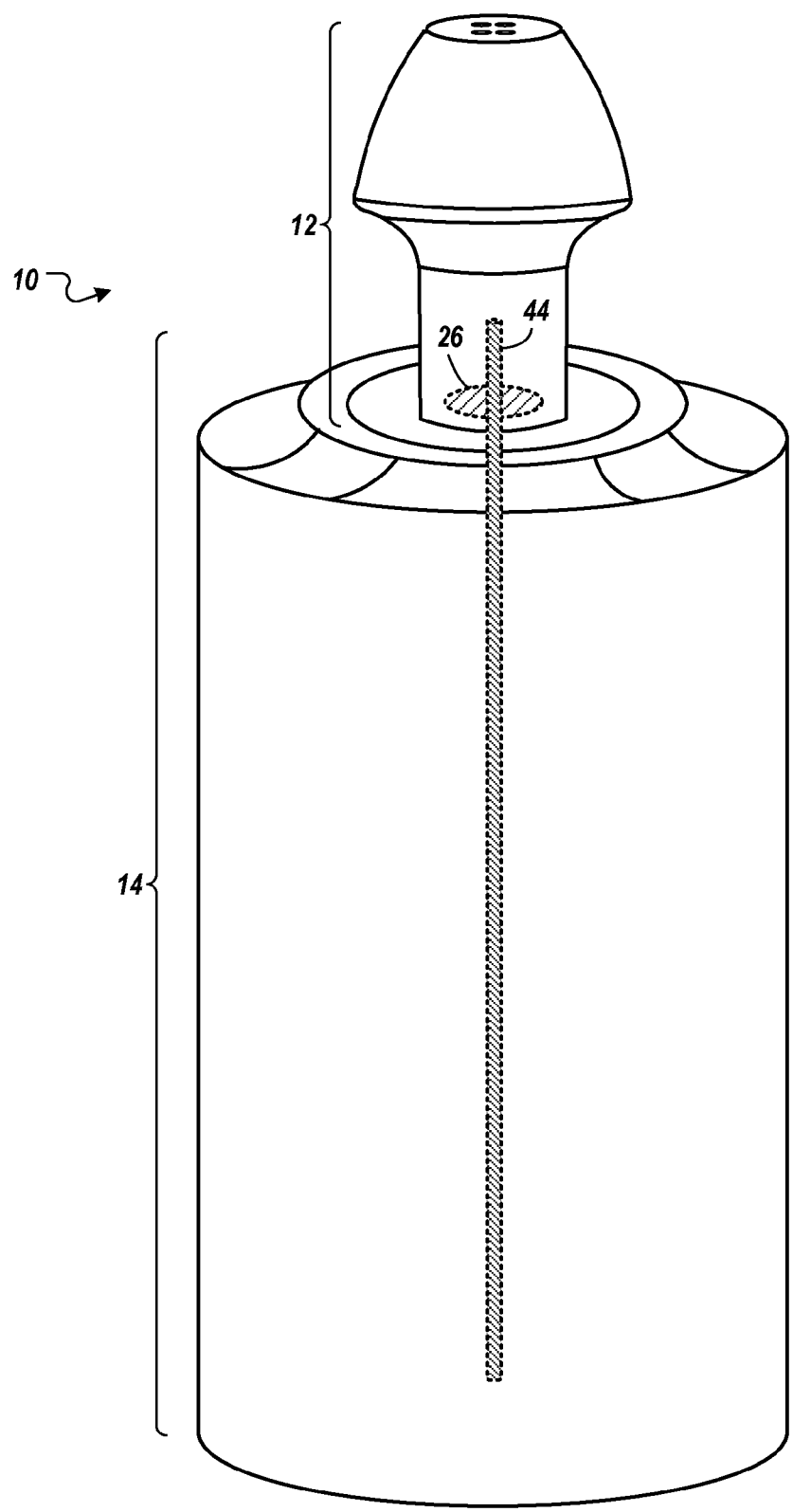
FIG. 7 is a schematic perspective view of the device.

Referring to FIG. 7, the fluid ejection device 10 is shown with the tip 12 covering the aperture 26 and the valve 42 which are both extruding from the body 14.

Figure 8:
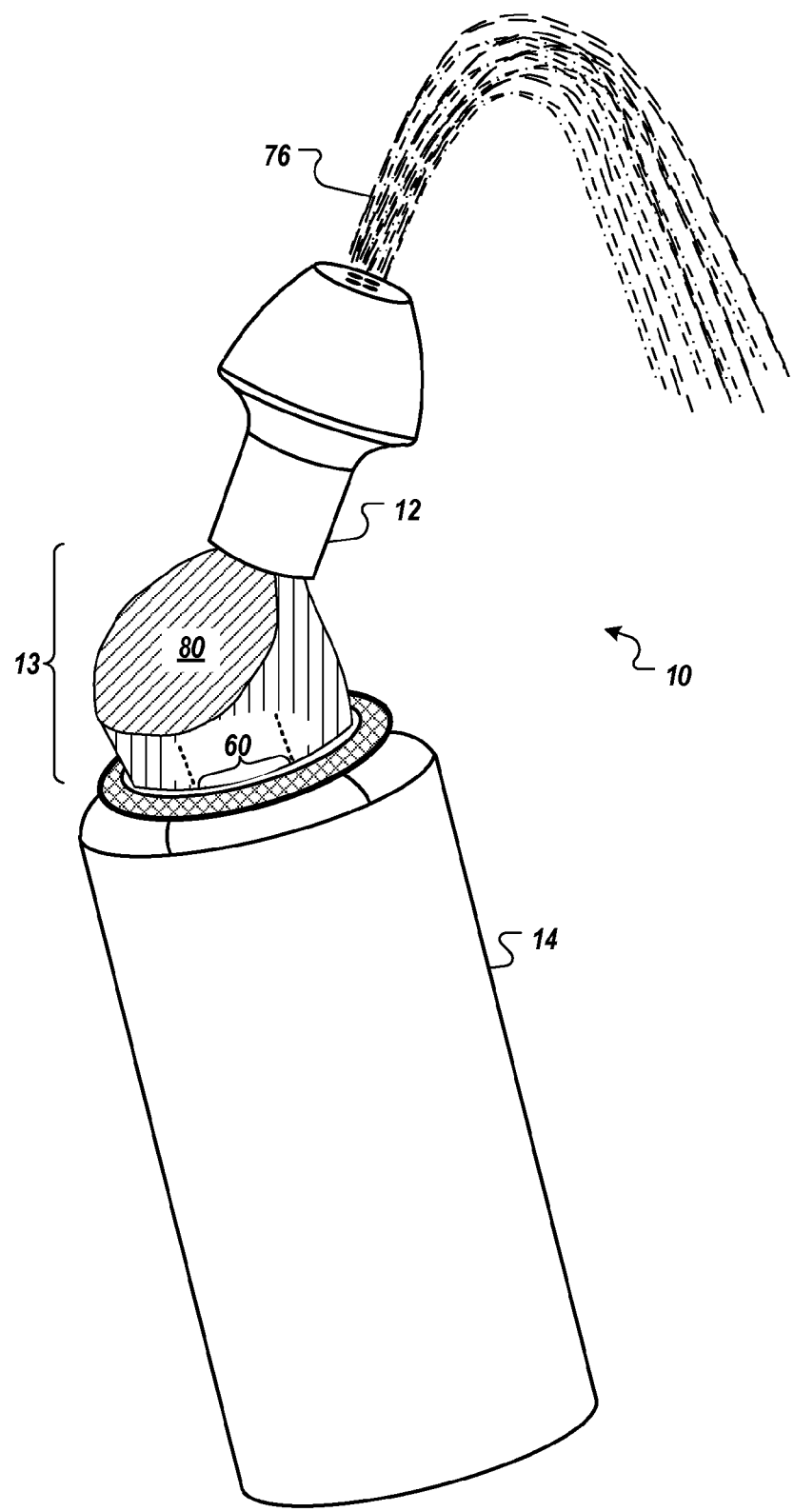
FIG. 8 is a schematic perspective view of the device in use.

Referring to FIG. 8, an exemplary stream of fluid 76 flowing from the fluid ejection device 10 is shown. The stream of fluid 76 can have a gentle arc, as depicted, due to the pressure-attenuating features of the tip 12. For example, while the fluid in the body 14 may be stored and released at a generally high pressure (e.g., too forceful for nasal lavage), the tip 12 can receive the fluid at high pressure, attenuate the pressure, and dispense the fluid at a lower pressure, but having a higher volume. In this way, the fluid stream can achieve an arc and flow as generally depicted by the stream of fluid 76. The stream of fluid 76 can exit the tip 12 along a trajectory that is along a central axis of the canal 60. The apex of the arc of fluid occurs within a range of between about 4 and 12 cm, such as 8 cm, such as within 7 cm or within 5 cm of the apertures. In some implementations, fluid is ejected in a stream rather than ejected as a mist or as individual droplets.

In some implementations, the tip 12 can include, or be fluidly connected to, the actuator 13 that can be used to start and stop the flow of fluid from the body 14. The actuator 13 depicted here in FIG. 8 is larger than the embodiment of the actuator 13 depicted in FIG. 1. As such, the tip 12 can connect directly to the larger actuator 13.

Figure 9:
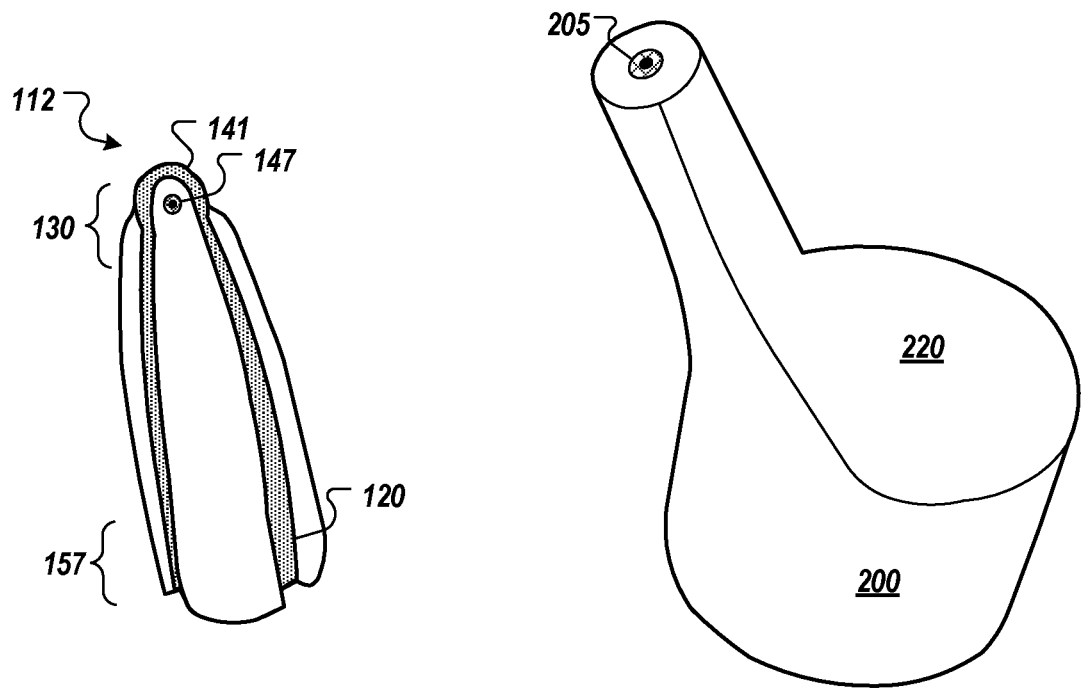
FIG. 9 is a perspective view of an implementation of a tip and actuator.
Figure 10:
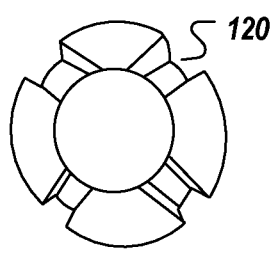
FIG. 10 is a top view of an implementation of a tip.

Referring to FIGS. 9 and 10, in some implementations, the tip 112 is approximately conically shaped from top to bottom. The tip 112 can have a base 157 with a circular inner diameter and an outer diameter that is either circular or approximately circular. Thus, the tip has an internal channel extending from the base 157 to an end upper region 130 of the tip 112. The tip 112 can include one or more grooves 120, such as two, three, four, five or six grooves. The grooves 120 can extend from the base 157 to the upper region 130 of the tip 112. In some implementations, the grooves extend at least 80% of the length of the tip 112. The tip has a thickness in the grooved area that is less than the thickness in the non-grooved area. Therefore, the grooved area can be more flexible than the non-grooved areas and can stretch more in a lateral direction, the lateral direction being perpendicular to the long axis of the internal channel, than the non-grooved areas.

Figure 11:
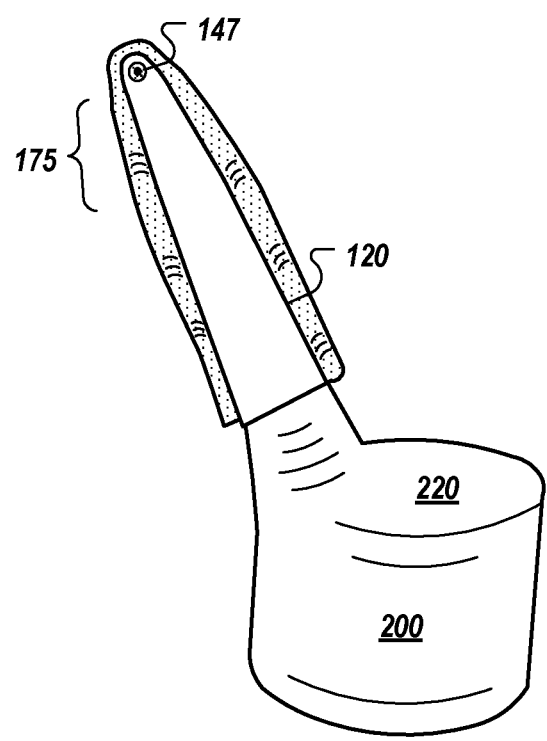
FIG. 11 is a side view of a tip on an actuator.

Referring to FIGS. 9 and 11, in some implementations, the upper region 130 of the tip has a smooth curved end 141. The upper region 130 of the tip can have one or more apertures 147 extending from the interior channel to the outer surface of the tip 112. In some implementations, the apertures 147 are not in the end 141, but are just below the end 141 and on the sides of the end 141. In some implementations, the apertures 147 are aligned with the thick portions of the tip 157 and not with the grooves 120. In some implementations, the tip 112 includes two apertures 147, each one directly across from one another so that the channel and the apertures together form a T-shape.

As with the first described tip, this tip can be formed of a flexible material, such as silicone or some another soft, flexible material (e.g., plastic, rubber, non-permeable cloth, etc.) that can generally feel comfortable against the user's skin. The actuator can be formed of a material that is significantly more rigid than the tip 112. As such, the actuator can hold its shape during use.

The tip 112 can fit over an actuator 200. The actuator can be similar to or the same as the actuator shown in FIG. 9. The actuator 200 has aperture 205 in its upper end. The aperture 205 is fluidly connected to a channel that extends the length of the actuator 200. The actuator 200 has a flat region 220 for depressing the actuator 200 and causing it to actuate a valve to which the channel is fluidly connected. The aperture 205 in the end of the actuator can be small, such as between 0.2 and 1 mm, e.g., around 0.4-0.6 mm in diameter. In some implementations, the aperture 205 in the actuator 200 is smaller than the apertures 147 in the tip 112.

Because of the flexibility of the tip 112, the tip can fit snugly around an end of the actuator. In some implementations, the snug fit is all around the circumference of the actuator. Thus, a liquid tight fit can be achieved around the actuator. In some implementations, at least 25%, such as at least 50%, for example, more than 60% of the tip length is over the actuator. This can prevent the tip from being pushed off of the actuator by the fluid pressure coming out of the dispenser. The shape of the actuator can be wider at the base than the tip. In some implementations, the tip has a cylindrical portion at a distal end, which transitions into widening portion that extends to the base. Because the tip can be flexible and stretch, the width of the tip can be equal to or smaller than the width of the actuator when the tip is not stretched or is in a relaxed state.

Between the end of the actuator and the apertures in the tip the channel forms a pocket 175 where fluid can pool before being pushed out of the apertures. The pocket 175 can have a length of between about 0.5 and 1.5 cm, such as around 1 cm. The pocket diameter can be between 0.2 and 0.6 cm.

In some implementations, the external diameter of the tip 112 at its base 157 is between 0.8 and 1.4 cm, such as between 0.9 and 1.2 cm. The thick regions of the tip 112 at the base 157 can be between 0.7 and 2 mm, such as around 1.7 mm. The thin regions, that is, the regions with the grooves, can be between 0.5 and 1 mm, such as about 0.7 or 0.8 mm. The length of the tip 112 can be between 2 and 5 cm, such as about 4 cm. The end of the tip 141 can be between 0.2 and 0.6 cm wide, such as about 0.4 cm. The apertures 147 can have a diameter of between about 0.6 and 1.5 mm, such as around 1 mm. The apertures 147 can be circular in shape.

Unlike the tip shown in FIG. 8, the tip with the apertures on a side surface of the tip causes fluid to exit the tip at approximately a right angle to the longest length of the tip.

During use of the fluid ejection device, a user can partially insert the tip into a nasal cavity. The fluid ejection device can be held, for example, is in the upright position, where the tip is generally above the body. Controlling the flow of fluid from the tip can be accomplished, for example, by pressing a flat-shaped button area, operable to engage (or disengage) the valve (not shown) inside the actuator when the button area is pressed (or released). This fashion of controlling fluid flow differs from that described with respect to FIG. 1 in which the entire tip can be pressed. In FIG. 1, fluid flow can be controlled, for example, by pressing downwardly or at an angle to a longitudinal axis of the tip. In some implementations, the tip can be pressed straight against the nose so that the actuator is effectively depressed, allowing the valve to open and fluid to flow from the tip. In some implementations, such as those shown in FIG. 8, the actuator can be depressed, such as with a finger, to cause solution to exit the tip. In other implementations, pressing the tip from the side actuates the valve and causes the fluid flow into the tip. Other implementations can include other controls, such as switches, levers, or electronic controls capable of opening and closing the valve. In some implementations, an additional control or button may exist that allows the valve to be locked in the open position. The tip can provide a gentler and more comfortable rinsing experience for a user.

A number of embodiments of the invention have been described. Nevertheless, it will be understood that various modifications may be made without departing from the spirit and scope of the invention. For example, instead of attenuating a fast stream of liquid into a gentle flow, a mist exiting the actuator can be transformed into a gentle cleansing stream of fluid. Accordingly, other embodiments are within the scope of the following claims.

What is claimed is:

1. A nasal rinse device, comprising:
a body surrounding a chamber;
a valve;
an actuator having a fluid path that is fluidly connected to the chamber when the valve is in an open position; and
a nasal rinse tip configured to redirect a flow of nasal rinse solution exiting the actuator as a spray,
wherein the nasal rinse tip has a distal portion and a proximate portion and defines an elongated interior cavity that is unobstructed along a longitudinal axis of the nasal rinse tip and that extends from an opening at the proximate portion toward a plurality of exit apertures at the distal portion, the distal portion defining a stop forming a flow obstruction positioned along the longitudinal axis of the nasal rinse tip so as to intercept the flow of nasal rinse solution as the flow of nasal rinse solution moves along the longitudinal axis of the nasal rinse tip and throughout the elongated interior cavity and so as to redirect the intercepted flow of nasal rinse solution around the flow obstruction and to the plurality of exit apertures for ejection.

2. The nasal rinse device of claim 1, wherein an exterior of the nasal rinse tip tapers outwardly between the distal portion and the proximate portion.

3. The nasal rinse device of claim 2, wherein the exterior is curved between the distal portion and the proximate portion.

4. The nasal rinse device of claim 1, wherein the distal portion defines an annular chamber connecting the flow obstruction and the plurality of exit apertures.

5. The nasal rinse device of claim 4, wherein a greatest extent of the plurality of exit apertures together is greater than an external circumference of the annular chamber.

6. The nasal rinse device of claim 5, further comprising a circular chamber between the elongated interior cavity and the annular chamber.

7. The nasal rinse device of claim 4, wherein the annular chamber has an external circumference that is greater than a circumference of the flow obstruction.

8. The nasal rinse device of claim 1, wherein the elongated interior cavity has a volume of at least 0.47 cm$^3$.

9. The nasal rinse device of claim 1, wherein the flow obstruction is positioned in line with the actuator, such that a longitudinal axis of the actuator extends through the flow obstruction.

10. A nasal rinse device, comprising:
a body surrounding a chamber, wherein the body is configured to resist a change in shape when a pressure change occurs within the body;
a valve;
an actuator having a fluid path that is fluidly connected to the chamber when the valve is in an open position; and
a nasal rinse tip configured to redirect a flow of nasal rinse solution exiting the actuator as a spray, wherein the nasal rinse tip defines multiple exit apertures in fluid communication with an elongated interior tip cavity into which the actuator extends, the elongated interior tip cavity being unobstructed along a longitudinal axis of the nasal rinse tip, and wherein the nasal rinse tip defines an internal stop forming a flow obstruction positioned along the longitudinal axis of the nasal rinse tip so as to intercept the flow of nasal rinse solution as the flow of nasal rinse solution moves along the longitudinal axis of the nasal rinse tip and throughout the elongated interior tip cavity and so as to redirect the intercepted flow of nasal rinse solution around a central portion of the flow obstruction and to the multiple exit apertures.

11. The nasal rinse device of claim 10, further comprising a tube within the chamber and connected to the valve.

12. The nasal rinse device of claim 11, further comprising a bag, wherein the bag comprises a flexible material, is within the body, and surrounds the tube, and wherein an interior of the bag is hermetically sealed from a space between the body and an exterior of the bag.

13. The nasal rinse device of claim 10, wherein the nasal rinse tip is formed of a flexible material.

14. The nasal rinse device of claim 13, wherein the nasal rinse tip is formed of silicone.

15. The nasal rinse device of claim 13, wherein the actuator is formed of a material that is more rigid than the nasal rinse tip.

16. The nasal rinse device of claim 13, wherein the nasal rinse tip has one or more grooves extending from an open proximal portion and at least 50% of a length of the nasal rinse tip.

17. The nasal rinse device of claim 16, wherein the multiple exit apertures comprise an aperture disposed along a side surface of the nasal rinse tip that is fluidly connected to the elongated interior tip cavity, the elongated interior tip cavity extending from the open proximal portion.

18. The nasal rinse device of claim 10, wherein the nasal rinse tip has an exterior circumference of less than 1.5 cm.

19. The nasal rinse device of claim 10, wherein the nasal rinse tip includes a flat exterior surface surrounding the multiple exit apertures.

20. The nasal rinse device of claim 19, wherein the nasal rinse tip includes a distal portion that tapers outwardly from the flat exterior surface to a proximate portion.

21. The nasal rinse device of claim 10, wherein the nasal rinse tip is configured to fit over a portion of the actuator extending from the body.

22. The nasal rinse device of claim 21, wherein the valve is configured to open upon a pressure being applied to the nasal rinse tip toward the body.

\* \* \* \* \*